(12) United States Patent
Hermelin et al.

(10) Patent No.: US 6,197,329 B1
(45) Date of Patent: Mar. 6, 2001

(54) ANTI-NAUSEA COMPOSITIONS AND METHODS

(75) Inventors: Marc S. Hermelin, Glendale; Mitchell I. Kirschner, St. Louis; R. Saul Levinson, Chesterfield, all of MO (US)

(73) Assignee: Drugtech Corporation, Wilmington, DE (US)

( * ) Notice: Subject to any disclaimer, the term of this patent is extended or adjusted under 35 U.S.C. 154(b) by 0 days.

(21) Appl. No.: 09/303,690

(22) Filed: May 3, 1999

(51) Int. Cl.[7] ............................. A61K 9/08; A61K 9/10; A61K 9/14; A61K 9/20; A61K 9/46; A61K 9/48

(52) U.S. Cl. .................. 424/441; 424/195.1; 424/464; 424/456; 424/466; 424/468; 424/472; 424/484; 424/489; 514/819; 514/872; 514/937

(58) Field of Search ................. 424/451, 456, 424/195.1, 441, 464, 465, 466, 468, 472, 484, 489; 514/819, 872, 937

(56) References Cited

U.S. PATENT DOCUMENTS

| | | | |
|---|---|---|---|
| 4,309,405 | 1/1982 | Guley et al. | 424/21 |
| 4,738,856 | 4/1988 | Clark | 426/74 |
| 4,786,505 | 11/1988 | Lovgren et al. | 424/468 |
| 4,806,354 | 2/1989 | Green | 424/154 |
| 4,853,230 | 8/1989 | Lovgren et al. | 424/466 |
| 4,925,878 | 5/1990 | Bodó et al. | 514/646 |
| 4,948,592 | 8/1990 | Ayer et al. | 424/473 |
| 4,994,283 | 2/1991 | Mehansho et al. | 426/74 |
| 5,578,628 | 11/1996 | Tyers et al. | 514/397 |
| 5,648,092 | 7/1997 | Weckenmann et al. | 424/464 |

OTHER PUBLICATIONS

*The Merck Manual*, p. 1281–87 (16th Ed. 1992).
*Drug Information for the Health Care Professional*, (17th Ed., 1997) 2179.
*Drug Information for the Health Care Professional*, (17th Ed., 1997) 1532.
Vutyavanich, et al., "Pyridoxine for nausea and vomiting in pregnancy: a randomized, double–blind, placebo–controlled trial", *Am J Obstet Gynecol*, 173:881–4 (1995).

*Primary Examiner*—James M. Spear
(74) *Attorney, Agent, or Firm*—Nath & Associates PLLC; Gary M. Nath

(57) ABSTRACT

The present disclosure is directed to novel nutritional anti-nausea compositions, anti-emetic compositions, and methods of using same. The compositions provide improved relief from nausea and/or vomiting. The compositions are particularly useful for pregnant women.

55 Claims, No Drawings

ANTI-NAUSEA COMPOSITIONS AND METHODS

BACKGROUND OF THE INVENTION

1. Field of the Invention

The present invention is directed to novel nutritional anti-nausea compositions, anti-emetic compositions and methods of using the same to provide relief from nausea and/or vomiting. The present compositions are also nonteratogenic and are therefore highly useful to pregnant women.

2. Description of the Related Art

Nausea and vomiting are two of the most common symptoms of illness and are also commonly experienced as side effects of numerous medical treatments. Both nausea and vomiting are also commonly experienced as a result of various external factors (e.g., travel) and during various conditions (e.g., pregnancy). Nausea and vomiting can occur individually or in conjunction with one another.

A common cause of nausea and vomiting is motion sickness. Motion sickness typically occurs when humans are subjected to long-lasting external movement or transportation accompanied by unusual movements such as shaking, waving, atmospheric changes (e.g., flying in an airplane), great acceleration, and uneven road conditions, etc. Motion sickness is not viewed as a disease but as a physiological symptom complex wherein the symptoms experienced, of which nausea and vomiting are common, depend on the individual in question. When the individual experiences motion sickness in a work environment, i.e., truck drivers, air pilots, air craft staff members and the like, the potential for a disadvantageous and dangerous condition result. Such individuals are often required to exhibit high level concentration and intellect, and the presence of motion sickness symptoms can severely detract from their ability to do so.

Though experienced by a more limited number of individuals, the nausea and vomiting associated with chemotherapy drugs and radiation treatment is especially problematic. Cancer treatment drugs such as Cisplatinum, Streptozotocin, Cytoxan, Nitrogen Mustard and Ara-C are known to cause severe nausea and vomiting as side effects. The reason that cancer drugs cause nausea and vomiting is still under investigation. It is believed that the drugs stimulate and irritate specific key areas in the brain which results in nausea and vomiting. Individuals undergoing cancer treatments and experiencing these side effects may feel discouragement beyond that which is directly related to their cancer. The inability to eat normally or to alleviate nausea can lead to increased patient depression. *The Merck Manual*, 1281–87 (16th Ed. 1992).

Postoperative nausea and vomiting is one of the most common side effects, estimated to be experienced by 20% to 30% of patients, after undergoing anesthetic and surgical procedures. Coates, A., "On the receiving end-patient perception of the side-effects of cancer chemotherapy", *Eur J Cancer Clin Oncol*, 19:203–208 (1983); See also, Cooper, et al., "The impact of cytotoxic chemotherapy-perspectives from patients, specialists and nurses", *Eur J Cancer Clin Oncol*, 28A(suppl 1):S36–S38 (1992). Research shows the occurrence of postoperative nausea and vomiting to be from 25% to 55% following inpatient surgery and from 8% to 47% for outpatient procedures. Id.; See also, Laszlo, J., "Nausea and vomiting as major complications of cancer chemotherapy", *Drugs*, 25(suppl 1):1–7 (1983); See also, Tortorice, et al., "Management of chemotherapy-induced nausea and vomiting", *Pharmacotherapy*, 10:129–145 (1990). When questioned prior to surgery, patients are often more concerned about post-operative nausea and vomiting than post-operative pain, since they perceive that the nausea and vomiting will be more debilitating. Tonato, et al., "Methodology of antiemetic trials: a review", *Ann Oncol*, 2:107–114 (1991); See also, Fauser, et al., "Therapeutic equivalence of single oral doses of dolasetron mesilate and multiple doses of ondansetron for the prevention of emesis after moderately emetogenic chemotherapy," *Eur J Cancer*, 32A(9):1523–1529 (1996).

Nausea and vomiting are also both common in early pregnancy. Cases can range in degree from mild to severe, and symptoms usually begin soon after the first missed period. Morning sickness, i.e., nausea and vomiting experienced during the first and second trimesters of pregnancy, is experienced by approximately half of all pregnant women, however it is particularly common in cases of multiple pregnancy and hydatidiform mole. Kousen, M., "Treatment of nausea and vomiting in pregnancy", *Am Fam Physician*, 48:1279 (1993).

Hyperemesis gravidarum, i.e., persistent nausea and vomiting during pregnancy, can lead to a reduction in fluid and electrolyte levels, as well as a jeopardized nutritional status if the condition is not treated. The condition is characterized by prolonged and severe nausea and vomiting, dehydration, ketosis, and body weight loss. Other complications may include hyponatraemia, hypokalaemia, a low serum level, metabolic hypochloraemic alkalosis, ketonuria, liver function test abnormalities, abnormal thyroid function tests, and suppressed thyroid-stimulating hormone levels. Nelson-Piercy, C., "Treatment of nausea and vomiting in pregnancy. When should it be treated and what can be safely taken?", *Drug Saf*, 19(2):155–64 (1998).

Nausea and vomiting can also be brought on by a variety of other causes such as reactions to certain types of odors or visual stimuli, psychological perceptions, allergic reactions, drug interactions and the like. Whatever the cause, the presence of a nauseated and/or emetic condition in an individual can be debilitating for the period during which it is experienced, and therefore numerous antiemetic and antinausea compositions and methods have been described.

Many generalized nausea and vomiting treatment compositions have been described. For example, Tyers et al., U.S. Pat. No. 5,578,628, describe tetrahydrocarbazolone derivatives which may be used for the prevention and treatment of nausea.

Lovgren et al., U.S. Pat. No. 4,786,505, describe a pharmaceutical preparation containing omeprazole for oral use and a method of affecting gastric acid secretion and providing gastrointestinal cytoprotective effect when using them.

Lovgren, U.S. Pat. No. 4,853,230, describes an easily water soluble pharmaceutical preparation containing an acid labile compound together with and alkaline reacting compound for the treatment of gastrointestinal diseases.

Bodó et al., U.S. Pat. No. 4,925,878, describe a composition especially suited for the treatment of the nausea and vomiting symptoms associated with motion sickness.

Numerous drugs have been developed for the treatment of chemotherapy-induced vomiting and nausea. Zofran®, a prescription antiemetic drug containing ondansetron as the active component, is a highly selective antagonist of serotonin receptors. Clinically accepted for use in treating cancer chemotherapy-induced nausea and vomiting, post-operative nausea and vomiting, and radiotherapy induced nausea and vomiting, this medication is not accepted for use in the treatment of motion-sickness or for prescription to pregnant or nursing women. *Drug Information for the Health Care Professional*, 2179 (17$^{th}$ Ed., 1997).

Kytril®, another prescription antiemetic, containing the active component granisetron, also works as a highly specific antagonist of serotonin receptors. Clinically, Kytril® is only accepted for use in treating cancer chemotherapy-induced nausea and vomiting and has not been proven safe for prescription to pregnant or nursing women. Id. at 1532.

In relation to the treatment of nausea and/or vomiting in pregnant women, different approaches have been attempted in order to avoid teratogenicity or at least reduce the risk of birth defects commonly associated with certain drugs for treating nausea and vomiting.

Studies have shown that certain vitamins may reduce nausea and/or vomiting. Administration of pyridoxine was shown to be effective in relieving the severity of nausea in early pregnancy without being teratogenic. Vutyavanich, et al., "Pyridoxine for nausea and vomiting in pregnancy:

a randomized, double-blind, placebo-controlled trial", *Am J Obstet Gynecol*, 173:881–4 (1995).

Further, it has been shown that the nausea and vomiting of pregnancy can be mitigated if the patient eats small portions of food at frequent intervals, increases the amount of carbohydrates, decreases the amount of fat, and avoids "bothersome food odors." Kousen, M., "Treatment of nausea and vomiting in pregnancy", *Am Fam Physician*, 48(7):1279–84 (1993).

Nutritional compositions for general improvement of health have been described in the related art. Green, U.S. Pat. No. 4,806,345, describes a health food composition which is comprised of B complex vitamins, i.e., thiamine, pyridoxine, riboflavin, and cyanocobalamin, an emulsifying agent, flavoring agent, a preservative agent and optionally an antacid such as calcium carbonate and/or an analgesic such as acetaminophen.

Meshansho, et al., U.S. Pat. No. 4,994,283, describe a nutritional composition comprised of iron compounds and calcium compounds in combination with citrates or tartrates, ascorbates, and, optionally, fructose.

Clark, U.S. Pat. No. 4,738,856, describes a yet another nutritional composition in the form of a beverage solution, which comprises calcium, magnesium, potassium, a sweetener agent and a stabilizer. The invention is specifically designed to have a reducing effect on conditions such as high blood pressure and high blood alcohol content.

It is generally accepted that it is of significant advantage under certain circumstances to both patients, physicians and nonpatients that medications and/or nutritional compositions be formulated so that they may be administered in a minimal number of daily doses from which the medication and/or nutritional composition is uniformly released over a desired, extended period of time. Such delivery methods are particularly useful for the sake of convenience when repeat dosing is necessary to bring about a desired therapeutic or physiological effect. Such delivery systems have been described.

Ayer et al., U.S. Pat. No. 4,948,592, describe a pulsed drug delivery system comprising an immediately available dose of a beneficial drug followed by a timed delayed dose of the drug, or simply a timed delayed dose of the drug.

Guley et al., U.S. Pat. No. 4,309,405, describe a sustained release tablet wherein the active drug in a core structure of the tablet surrounded by a water soluble polymer such hydroxypropylmethylcellulose or hydroxypropylcellulose and a water insoluble polymer such as ethylcellulose.

Another form of drug delivery which has been accepted as useful to both patients, physicians and nonpatients is the chewable tablet dosage form. This type of dosing finds particular applicability in persons who have difficulty swallowing tablet-type forms of medications and/or nutritional compositions or when the substance contained within the tablet is most beneficial when delivered immediately, such as with antacid formulations. Chewable tablets forms have been described in the art.

Weckenamnn et al., U.S. Pat. No. 5,648,092, describe pharmaceutical compositions in the form of pleasant tasting chewable tablets containing sulcralfate, which is employed for the treatment of duodenal ulcers, gastric ulcers and reflux esophagitis.

While numerous antiemetic compositions and methods exist, these compositions often produce numerous and undesired patient side-effects. These formulation have the result of placing the patient in the position of choosing between the condition she or he seeks to alleviate and the side effect of the therapy. Further, these formulations do not utilize vitamins and minerals as active components, and therefore have no direct positive impact on the patient's nutritional status. Thus, it is desirable to have effective antiemetic formulations which have few side effects and are nutritionally beneficial to the taker.

The disclosed antiemetic compositions are deficient in various other respects. Primarily, none have undergone extensive clinical studies on humans with regards to teratogenicity, and thus are not recommended for ingestion by pregnant women except for in the most extreme of situations. Even the above discussed references which recognize the potential for teratogenicity, and thus seek to provide for alternative methods of treatment, do not specifically disclose distinct nutritional formulations for treating nausea and vomiting. Further these references do not provide any guidance with regard to formulating nutritional compositions for treating nausea and vomiting.

Therefore, it is desirable to have formulations available which are effective in providing relief to nausea and vomiting arising from various causes. Moreover, there is a particular need for formulations which simultaneously relieve nausea and/or vomiting and provide a higher degree of patient compliance and are available at minimal cost. Additionally, there remains a need for specific nutritional formulations which have an antiemetic effect, are nonteratogenic, and also support good health. It is also particularly desirable to have formulations available which minimize the need to take medications and which are suitable to be taken by individuals who seek to limit their use of medications. Thus, there is a general overall need for a fundamentally new, safe, effective and comprehensive approach to addressing the treatment of nausea and vomiting arising from various causes.

SUMMARY OF THE INVENTION

The present invention overcomes the deficiencies of currently available antiemitic and antinausea compositions in a number of ways. First, the present nutritional compositions do not possess teratogenic characteristics. The present invention also can be taken in conjunction with medications and presents minimal risk of interaction. Furthermore, the formulations of the invention have been found to reduce the occurrence of nausea and vomiting in pregnant women experiencing morning sickness or hyperemisis gravidarum and in persons undergoing cancer treatments such as chemotherapy or radiation therapy. The compositions of the invention also include method of dosing, i.e., pulsed delivery or chewable, which present useful and convenient options for the patient, physician and nonpatient.

Thus, the invention provides for anti-nausea nutritional compositions which are designed to provide relief from nausea when administered to an animal, i.e., human, mammal or any other animal, which comprises a vitamin $B_6$ compound or derivative thereof in an amount ranging from about 20 mg to 125 mg per 55 kg of body weight; an alkaline buffering agent in an amount sufficient to provide a pH buffering effect in said animal's gastrointestinal tract; an acceptable coating agent; and wherein the vitamin $B_6$ compound or derivative thereof is separated from the alkaline buffering agent by said acceptable coating agent.

The invention also provides for a solid anti-nausea nutritional composition which is designed to provide relief from nausea when administered to an animal, which comprises: a vitamin $B_6$ compound or derivative thereof in an amount ranging from about 20 mg to 125 mg per 55 kg of body weight; and an alkaline buffering agent in an amount sufficient to provide a pH buffering effect in said animal's gastrointestinal tract.

The invention further provides for an anti-nausea nutritional composition which is designed to provide relief from nausea when administered to an animal, which comprises: a vitamin $B_6$ compound or derivative thereof in an amount ranging from about 20 mg to 125 mg per 55 kg of body weight; a folic acid compound or derivative thereof in an amount ranging from about 0.1 mg to 2 mg per 55 kg of body weight; an alkaline buffering agent in an amount sufficient to provide a pH buffering effect in said animal's gastrointestinal tract; an acceptable coating agent; and wherein the vitamin $B_6$ is separated from the alkaline buffering agent by said acceptable coating agent.

The invention additionally provides for an anti-nausea nutritional composition which is designed to provide relief from nausea when administered to an animal, which comprises: a vitamin $B_6$ compound or derivative thereof in an amount ranging from about 20 mg to 125 mg per 55 kg of body weight; an alkaline buffering agent in an amount sufficient to provide a pH buffering effect in said animal's gastrointestinal tract; and means for providing pulsed or timed delayed dosing of said vitamin $B_6$ compound or derivative thereof and said alkaline buffering agent.

The invention further provides for an anti-nausea and antiemetic nutritional composition which is designed to provide relief from nausea and vomiting when administered to an animal, which comprises: a vitamin $B_6$ compound or derivative thereof in an amount ranging from about 20 mg to 125 mg per 55 kg of body weight; and an alkaline buffering agent in an amount sufficient to provide a pH buffering effect in said animal's gastrointestinal tract.

The invention likewise provides for an anti-nausea nutritional composition which is designed to provide relief from nausea when administered to an animal, which comprises: a vitamin $B_6$ compound or derivative thereof in an amount ranging from about 20 mg to 125 mg per 55 kg of said animal's body weight; an alkaline buffering agent in an amount sufficient to provide a pH buffering effect in said animal's gastrointestinal tract; and a B vitamin selected from the group consisting of thiamin, riboflavin, niacin, biotin, pantothenic acid, folate, folic acid, and cobalamin.

The invention also provides a method for treating nausea in an animal, which comprises: administering to said animal a therapeutically effective amount of a composition comprising: a vitamin $B_6$ compound or derivative thereof in an amount ranging from about 20 mg to 125 mg per 55 kg of body weight; an alkaline buffering agent in an amount sufficient to provide a pH buffering effect in said animal's gastrointestinal tract; an acceptable coating agent; and wherein the vitamin $B_6$ is separated from the alkaline buffering agent by said acceptable coating agent.

Another aspect of the present invention is a method for treating nausea or vomiting in a pregnant woman, which comprises: administering to said pregnant woman a therapeutically effective amount of a composition comprising a vitamin $B_6$ compound or derivative thereof in combination with an alkaline buffering agent.

A further aspect of the invention is a method for treating nausea in a pregnant woman, which comprises: administering to said pregnant woman a therapeutically effective amount of a composition comprising a vitamin $B_6$ compound or derivative thereof in combination with an alkaline buffering agent; and simultaneously applying controlled pressure to an acupressure site on said pregnant woman.

A still further aspect of the invention is a method for treating hyperemesis gravidarum in a pregnant woman, which comprises: administering to said pregnant woman a therapeutically effective amount of a composition comprising a vitamin $B_6$ compound or derivative thereof in combination with an alkaline buffering agent.

The invention likewise provides for a method for preventing the nausea associated with pregnancy, which comprises administering a vitamin $B_6$ compound or derivative thereof in an amount ranging from about 20 mg to 125 mg per 55 kg of said animal's body weight and an alkaline buffering agent in an amount sufficient to provide a pH buffering effect in said animal's gastrointestinal tract in combination with a prenatal vitamin regimen.

Another embodiment of the invention is a kit for treating nausea or vomiting in an animal, which comprises: a vitamin $B_6$ compound or derivative thereof in combination with an alkaline buffering agent; and an apparatus for applying controlled pressure to an acupressure site on said animal.

DETAILED DESCRIPTION OF THE INVENTION

As used herein, "continuous nausea relief" refers to the alleviation of the symptom of nausea during each 24 hour period of time during which the present compositions are administered.

"Continuous vomiting relief" refers to the alleviation of the symptom of vomiting during each 24 hour period of time during which the present compositions are administered.

"Animal" refers to a human, mammal or any other animal.

"Nausea associated with pregnancy" refers to morning sickness, evening sickness and hyperemesis gravidarum, without limitation.

"Pulsed delivery" refers to a delivery method which supplies repetitive doses of a composition from a single administration.

"Timed delivery" refers to a delivery method which supplies repetitive doses of a composition in pre-determined amounts at pre-determined times after administration.

"Targeted time period" refers to the period of time during which nausea and vomiting are anticipated or expected to occur.

"Targeted time delivery" refers to a delivery method which supplies a dosage or dosages of the composition in conjunction with the occurrence of the period of time during which nausea and vomiting are anticipated or expected to occur.

The present invention is based in part on the discovery that certain vitamins, minerals and other nutrients and their components and compositions can produce specific physiological effects beyond their usual function of maintaining good health and well being. Specifically, certain conditions are treatable with the administration of certain nutritional compositions. Furthermore, in some cases treatment of specific conditions with nutritional compositions, as opposed to pharmaceutical compositions, is quite desirable due to the fact that nutritional compositions produce few side effects and along with treating the condition in question, nutritional compositions have positive effects upon the taker's health. Moreover, the present invention is based, in part, upon the realization that the type of dosage form used with the specific nutritional component is significant and can result in synergistically improved efficacy. The present compositions are particularly effective when formulated into a pulsed release dosage form.

The present inventive subject matter recognizes that there are substantial physiological benefits to be attained from specific formulations of vitamins and minerals to person who are experiencing nausea and/or vomiting.

The present compositions and methods are also effective in preventing and treating nausea and/or vomiting in persons undergoing medical treatment involving drugs which may negatively interact with prescription gastric neutralizing agents, as well as persons simply seeking to minimize medication intakes.

Furthermore, pregnant women, who comprise a large portion of the individuals who experience nausea and vomiting, must be cautious of teratogenic substances, such as those potentially contained in other anti-nausea and anti-emetic compositions. Thus, pregnant women should avoid such compositions and seek out treatments which are accepted as nonteratogenic. The products of the invention provide for nutritional compositions which provide relief from nausea and vomiting and are accepted as nonteratogenic. Thus, the products of the invention are ideal for administration to pregnant women.

Furthermore, the present inventive subject matter recognizes the corollary benefits of the administration of antinausea and antiemetic compositions in a preventative manner. A patient who believes that he or she will be subject to the conditions of nausea and vomiting in the future may experience mental stress and/or anxiety based upon this belief. For example, a person with a history of motion sickness may be reluctant to travel, even for pleasure, because the motion sickness detracts from the positive aspects of the experience. Thus, such a person may become distressed at the contemplation of travel wherein his or her presence is required or mandated, i.e., a family or business related trip.

Likewise, a pregnant woman, who is prone to but not currently experiencing morning sickness, may feel a certain sense of foreboding. She is well aware that in the near future she will become nauseous and vomit despite the fact she presently feels normal. Such knowledge detracts from her current peace of mind and may lead to anxiety. By administering the compositions of the present invention in a prophylactic manner, individuals similar to the ones described may experience a certain sense of calm and increased well being, as well as a reduction in anxiety, due to the fact that they have been able to take a pro-active course of action with regards to their conditions.

Without being limited by theory, the compositions, methods and kits of the present invention may be effective because they provide vitamins, minerals and other nutrients which mitigate nausea and vomiting. Alternatively, the compositions and methods may be effective because they aid in the metabolic processes and/or other physiological reactions which prevent nausea and vomiting.

The nutritional compositions of the present invention contain specific concentrations of vitamins and minerals for administration to individuals currently experiencing nausea and vomiting, individuals predisposed to nausea and vomiting, or individuals who would reasonably anticipate such symptoms in the near future. The compositions of the invention also provide safe and effective vitamins and minerals which are recognized as required in daily amounts by humans, and thus are beneficial to overall health.

The nutritional compositions of the present invention may be formulated to provide continuous relief from nausea. The nature of the continuous relief is brought about from the time the individual begins metabolizing the first dosage of the composition during the twenty four hours or a lesser time than twenty four hours after the time the individual ceases use. Therefore, the alleviation of the symptoms will be constant throughout each twenty four hour period or a lesser time than twenty four hours during the entire time which the nutritional composition is taken on a regular daily basis.

For example, if an individual takes the nutritional compositions for a period of a month, the individual could expect to experience greatly reduced occurrences of nausea during the entire duration of the month period.

Furthermore, the compositions of the present invention may be formulated to provide short term relief from nausea as well. For example, an individual who anticipates experiencing nausea in the near future for a defined period of time, (e.g., during a boat ride) would benefit from ingesting the nutritional compositions of the present invention prior to this period of time. Further, this individual could expect to receive relief from the anticipated symptoms. The short term relief mechanism of this composition can also be utilized to provide relief from symptoms which the individual is presently experiencing. For example, an individual could ingest the compositions of the present invention while experiencing nausea in order to obtain relief from the symptoms.

The nutritional compositions of the present invention are nonemetic, are formulated to act as anti-emetics and may provide continuous relief from vomiting. Here again, the continuous nature of the relief is affected from the time metabolization of the first dosage begins and lasts until about twenty four hours or a lesser time than twenty four hours after the time subsequent dosages are ceased, thus alleviating the symptoms for the period of time during when the nutritional composition is taken regularly.

Additionally, the nutritional compositions of the present invention can provide short term relief from vomiting, either on an anticipatory basis, i.e., the individual expects to vomit, or on an alleviatory basis, i.e., the individual is currently experiencing the symptom of vomiting.

The present invention is also composed of accepted nonteratogenic compositions and is therefore safe for ingestion by pregnant women without fear of adverse affects (e.g., birth defects) upon the unborn child. Furthermore, a women who believes she may become pregnant or has recently learned that she is pregnant, could begin a regimen of the nutritional compositions of the present invention, either alone or in conjunction with a prenatal vitamin regime, in order to avoid the onset of symptoms of morning sickness and other forms of nausea associated with pregnancy.

The nutritional compositions of the present invention are formulated to mitigate and/or alleviate nausea and vomiting. The extent to which the nausea and vomiting are mitigated and/or alleviated may be influenced by numerous external factors, such as the following, non-limiting examples: diet, alcohol consumption, drug use, poor compliance and the like. Moreover, the effectiveness of the compositions may vary from individual to individual for a wide variety of reasons, such as genetic predisposition, health factors, and the like, without limitation.

The formulations of the present invention contain vitamin $B_6$ (pyridoxine) or derivatives thereof. Derivatives of vitamin $B_6$ include compounds formed from vitamin $B_6$ which are structurally distinct from vitamin $B_6$, but which retain the active function of vitamin $B_6$. Such derivatives include, without limitation, pyridoxine, pyridoxal, pyridoxamine, pyridoxal phosphate, salts of vitamin $B_6$, chelates of vitamin $B_6$, combinations thereof and the like. The vitamin $B_6$ may be present in a single form or in various different forms in combination within the present compositions. The specific amount of vitamin $B_6$ in the compositions is adjusted based on the type of dosage form utilized (i.e., immediate release vs. controlled release) and tablet type (i.e., chewable).

In the case of the immediate release compositions, the amounts of vitamin $B_6$ in the compositions preferably range from about 10 mg to about 135 mg per 55 kg of body weight. More preferably, the amounts of vitamin $B_6$ in the immediate release compositions range from about 15 mg to 130 mg per 55 kg of body weight. Even more preferably, the amounts of vitamin $B_6$ in the immediate release compositions range from about 20 mg to about 125 mg per 55 kg of body weight.

The amount of vitamin $B_6$ present in the controlled release compositions of the present invention, preferably range from about 65 mg to about 135 mg per 55 kg of body weight. More preferably, the amounts of the vitamin $B_6$ present in the controlled release compositions range from about 70 mg to about 130 mg per 55 kg of body weight. Most preferably, the amounts of vitamin $B_6$ in the controlled releases compositions range from about 120 mg to about 125 mg per 55 kg of body weight.

The amount of vitamin $B_6$ present in the chewable tablet type of the present invention, preferably ranges from about 25 mg to about 75 mg per 55 kg of body weight. More preferably, the amounts of vitamin $B_6$ present in the controlled release compositions range from about 40 mg to about 60 mg per 55 kg of body weight. Most preferably, the amounts of vitamin $B_6$ in the controlled releases compositions range from about 45 mg to about 55 mg per 55 kg of body weight.

The compositions of the present invention may include a folic acid compound or derivative thereof. The derivatives of folic acid include compounds formed from folic acid which are structurally distinct from folic acid, but which retain the active function of folic acid. Non-limiting examples of such derivatives include folate, folacin, pteroylglutamic acid, dihydrofolate, tetrahydrofolate, salts of folic acid, chelates of folic acid, combinations thereof and the like. Preferably, the amounts of folic acid in the immediate release compositions of the invention range from about 0.01 mg to about 3 mg per 55 kg of body weight of folic acid compound or derivative. Most preferably, the amounts of folic acid in the invention range from about 0.1 mg to about 2.0 mg per 55 kg of body weight. The amounts of folic acid in the controlled release compositions of the invention preferably range from about 0.1 mg to about 3 mg per 55 kg of body weight. More preferably, the amounts of folic acid in the controlled release compositions range from about 0.5 mg to about 1.5 mg per 55 kg of body weight. Note that the amount of folic acid does not vary when the nutritional composition is in chewable tablet type form.

The compositions of the present invention may optionally include a vitamin $B_{12}$ compound or derivative thereof. The derivatives of vitamin $B_{12}$ include compounds formed from vitamin $B_{12}$ which are structurally distinct from vitamin $B_{12}$, but which retain the active function of vitamin $B_{12}$. Non-limiting examples of such derivatives include methylcobalamin, deoxyadenosylobalamin, salts of vitamin $B_{12}$, chelates of vitamin $B_{12}$, combinations thereof and the like. Preferably, the amounts of vitamin $B_{12}$ in the immediate release compositions of the invention range from about 10 mg to about 15 mg per 55 kg of body weight of vitamin $B_{12}$ compound or derivative.

Similarly, the amounts of vitamin $B_{12}$ in the controlled release compositions of the invention preferably range from about 10 mg to about 15 mg per 55 kg of body weight.

The compositions of the invention may contain any additional vitamin, pharmaceutically acceptable mineral compound, or derivative thereof. Non-limiting exemplary vitamins for incorporation into the present invention include thiamin, riboflavin, niacin, biotin, pantothenic acid, folate, folic acid, cobalamin and combinations thereof. Non-limiting exemplary derivatives of vitamin compounds include salts, alkaline salts, esters and chelates of any vitamin compounds.

The compositions of the present invention may optionally include a calcium carbonate compound or derivative thereof. Preferably, the amounts of calcium carbonate in the compositions of the invention range from about 100 mg to about 550 mg per 55 kg of body weight of calcium carbonate compound or derivative. Even more preferably, the amounts of calcium carbonate in the compositions of the invention range from about 150 mg to about 500 mg per 55 kg of body weight. Most preferably, the amounts of calcium carbonate in the invention range from about 200 mg to about 450 mg per 55 kg of body weight. Note that the amount of calcium carbonate does not necessarily vary in the nutritional composition with regards to immediate vs. controlled release or in the chewable tablet form.

The compositions of the present invention may optionally include one or more of the following: thiamin, thiamin pyrophosphate, riboflavin, flavin mononucleotide, flavin adenine dinucleotide, niacin, nicotinic acid, nicotinamide, niacinamide, nicotinamide adenine dinucleotide, tryptophan, biotin, pantothenic acid, ascorbic acid, retinol, retinal, retinoic acid, beta-carotene, 1,25-dihydroxycholecalciferol, 7-dehyrdocholesterol, alpha-tocopherol, tocopherol, tocotrienol, menadione, menaquinone, phylloquinone, naphthoquinone, phosphorus, potassium, sulfur, sodium, docusate sodium, chloride, magnesium, copper, iodine, zinc, chromium, molybdenum, and iron.

The compositions of the present invention contain an alkaline buffering agent. The alkaline buffering agent may be selected from the following non-limiting examples: aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

Preferably, the amounts of alkaline buffering agent in the compositions of the invention range from about 100 mg to about 300 mg per 55 kg of body weight of alkaline buffering compound or derivative. Even more preferably, the amounts of calcium carbonate in the compositions of the invention range from about 150 mg to about 250 mg per 55 kg of body weight.

The nutritional compositions of the present invention have a low moisture content. Preferably, the nutritional compositions of the present invention have a moisture content of less than 5%. More preferably, the moisture content is less than 2.5%. Even more preferably, the moisture content is less than 2%. Most preferably, the moisture content is less than 1%.

The nutritional compositions of the present invention may also optionally include coating agents. Acceptable coating agents may be selected from the following, without limitation: cellulose dibutylaminohydroxypropyl ether, polyvinyl acetal diethylamino acetate, 2-methyl-5-vinylpyridine methacrylate-methacrylic acid copolymer, hydroxypropyl methyl cellulose phthalate, hydroxypropyl methyl cellulose acetate succinate, ethyl cellulose, cellulose acetate, cellulose acetate phthalate, cellulose propionate, cellulose butyratem cellulose valerate, cellulose acetate propionate, polyvinyl acetate, polyvinyl acetate phthaalate, polyvinyl formal, polyvinyl butyral, ladder polymer of sesquiphenyl siloxane, polymethyl methacrylate, poly carbonate, polystyrene, polyester, cumaroneindene polymer, polybutadiene, vinyl chloride-vinyl acetate copolymer, ethylene-vinyl acetate copolymer, vinyl chloride-propylene-vinyl acetate copolymer, poly(methacrylic acid, methyl methacrylate) 1:1, poly(methacrylic acid, ethyl acrylate) 1:1, beef tallow, whale wax, bees wax, paraffin wax, castor wax, myristic, palmitic, stearic and behenic acids, esters thereof and combinations thereof.

It is also possible in the nutritional composition of the present invention for the dosage form to combine various forms of release, which include, without limitation, immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is performed using well known procedures and techniques available to the ordinary artisan. Each of these specific techniques or procedures does not constitute an inventive aspect of this invention.

Any pharmaceutically acceptable dosage form, as well as combinations thereof, is contemplated by the invention. Examples of such dosage forms include, without limitation, compressed tablets, film coated tablets, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, dispersible granules, cachets, douches, suppositories, creams, topicals, inhalants, aerosols inhalants, patches, particle inhalants, implants, depot implants, ingestibles, injectables, infusions, health bars, liquids, animal feeds, cereal coatings, cereals, confections, foods, nutritive foods, functional foods and combinations thereof. The preparation of any of the above dosage forms is well known in the art.

The following represent examples, without limitation, of acceptable methods of preparing some of the above-listed dosage forms. For example, animal feed may be by methods well known to persons of ordinary skill in the art. Animal feeds may be prepared by mixing the formulation with binding ingredients to form a plastic mass. The mass is then extruded under high pressure to form tubular (or "spaghetti-like") structures that are cut to pellet size and dried.

Quick dissolve tablets may be prepared, for example, without limitation, by mixing the formulation with agents such as sugars and cellulose derivatives, which promote dissolution or disintegration of the resultant tablet after oral administration, usually within 30 seconds.

Cereal coatings may be prepared, for example, without limitation, by passing the cereal formulation, after it has been formed into pellets, flakes, or other geometric shapes, under a precision spray coating device to deposit a film of active ingredients, plus excipients onto the surface of the formed elements. The units thus treated are then dried to form a cereal coating.

For example, health bars may be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example, without limitation, may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are well versed in the processes and the machinery used as the chewable dosage form is a very common dosage form in the pharmaceutical industry.

Film coated tablets, for example, without limitation, may be prepared by coating tablets using techniques such as rotating pan coating methods or air suspension methods to deposit a contiguous film layer on a tablet. This procedure is often done to improve the aesthetic appearance of tablets, but may also be done to improve the swallowing of tablets, or to mask an obnoxious odor or taste, or to improve to usual properties of an unsightly uncoated tablet.

Compressed tablets, for example, without limitation, may be prepared by mixing the formulation with excipients intended to add binding qualities to disintegration qualities. The mixture is either directly compressed or granulated then compressed using methods and machinery quite well known to those in the industry. The resultant compressed tablet dosage units are then packaged according to market need, i.e., unit dose, rolls, bulk bottles, blister packs, etc.

The present nutritional compositions are formulated for administration by any route, including without limitation, oral, buccal, sublingual, rectal, parenteral, topical, inhalational, injectable and transdermal. The physicochemical properties of nutritional compositions, their formulations, and the routes of administration are important in absorption. Absorption refers to the process of nutritional composition movement from the site of administration toward the systemic circulation. Most orally administered nutritional compositions are in the form of tablets or capsules primarily for convenience, economy, stability, and patient acceptance. They must disintegrate and dissolve before absorption can occur. Using the present invention with any of the above routes of administration or dosage forms is performed using well known procedures and techniques available to the ordinary skilled artisan.

The present invention uses pharmaceutically acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art, and combinations thereof. Exemplary non-limiting solvents are water, ethanol, isopropyl alcohol, methylene chloride or mixtures and combinations thereof. Exemplary non-limiting bulking substances include sugar, lactose, gelatin, starch, silicon dioxide and combinations thereof.

The plasticizers used in the dissolution modifying system are preferably previously dissolved in an organic solvent and added in solution form. Preferred plasticizers may be selected from the group consisting of diethyl phthalate, diethyl sebacate, triethyl citrate, cronotic acid, propylene glycol, butyl phthalate, dibutyl sebacate, caster oil and mixtures thereof, without limitation. As is evident, the plasticizers may be hydrophobic as well as hydrophilic in nature. Water-insoluable hydrophobic substances, such as diethyl phthalate, diethyl sebacate and caster oil are used to delay the release of water-soluble vitamins, such as vitamin $B_6$ and vitamin C. In contrast, hydrophilic plasticizers are used when water-insoluble vitamins are employed which aid in dissolving the encapsulated film, making channels in the surface, which aid in nutritional composition release.

The compositions of the present invention are intended for use by humans and other animals, and both males and females. The dosages are adjusted according to body weight and thus are set forth herein on a per body weight basis. For example, where the formula specifies a range of 20–125 mg for a 55 kg individual, that range would be adjusted for a 35 kg individual to 13–80 mg (e.g., the lower range limit=(35 kg/55 kg)*20 mg=12.6 mg, or about 13 mg). Decimal amount may be rounded to the nearest whole number. In the above manner, the present compositions may be thus adapted to be suitable for any individual regardless of size.

Further, the dosages may be adjusted to compensate for differences in physiological need, including without limitation differing physiological needs of women and men. Moreover, the formulations can be further adapted based upon the specific needs, genetic predispositions or identified deficiencies of the individual trying to conceive. Moreover, the present compositions can be used as one component of a prescribed therapy.

The dosage forms of the present invention may involve the administration of a nutritional composition in a partial, i.e., fractional dose, one or more times during a 24 hour period, e.g., a single dose during a 24 hour period of time, or a multiple dose during a 24 hour period of time.

The methods of the invention are applicable to males and females. The methods are also applicable to healthy and ill individuals, and are particularly suitable for individuals with heightened susceptibility to nausea and vomiting (e.g., pregnant woman, persons undergoing chemotherapy, etc.). The methods of the invention may be used alone or in combination with other therapies. For example, without limitation, the methods may involve the administration of the present compositions to pregnant women in combination with their prenatal vitamin regimen or may involve administration of the present compositions to post-operative patients along with pain medication. Thus, the methods would have prophylactic effect for individuals with higher susceptibility to nausea and/or vomiting. Additionally, the present invention may involve targeting specific time periods during which nausea can be most expected. By targeting specific time periods during which nausea or vomiting are most likely to occur with a drug delivery system, such as pulsed or delayed release, without limitation, relief from nausea or vomiting relief is unexpectedly higher than when targeted time delivery is not used.

Further, in the previously stated preferred embodiments, the present invention may involve the application of a controlled amount of pressure to acupressure points, for example, without limitation, Neiguan acupressure points on both forearms of the patient. This may be achieved in various manners, for example, without limitation, by use of one or more pressure applying apparatuses, are adapted to be secured to the patient's arms, for example, without limitation, in the general manner of a watch band.

Acupressure is a derivative technique of acupuncture, which is the Chinese method of pricking the body with needles at specific predetermined points or locations in order to relieve pain and/or cure disease. In acupressure, pressure is applied to the specific predetermined points or locations on the body, and no needles are used. One example of a specific predetermined point is the Neiguan point, which is located on the flexor side of the forearm just above the wrist. The Neiguan point is utilized in acupressure as a means of providing relief for nausea and vomiting.

The present invention has numerous ancillary benefits, for example, without limitation, the present invention provides, in addition to relief from nausea or vomiting, the nutritional benefits inherent in vitamin and mineral supplementation. The present invention is also beneficial psychologically for individuals who anticipate nausea or vomiting in that it alleviates concern, relaxes and provides confidence to such individuals.

The constituents of the invention being thus described, the following represent examples of possible formulations and methods of manufacturing the present invention. The following examples are illustrative of preferred embodiments of the invention and are not to be construed as limiting the invention thereto.

EXAMPLES

Components of Anti-Nausea Compositions

Example 1

The following compositions are used to prepare anti-nausea products for administration to persons experiencing the symptoms of nausea.

TABLE I

| COMPONENT | FORMULA I | FORMULA II | CHEWABLE FORMULA | CONTROLLED RELEASE |
|---|---|---|---|---|
| Vitamin $B_6$, mg | 20–50 | 75–125 | 50–75 | 75–125 |
| Folic Acid, mg | — | 0.1–2 | 0.1–500 | 0.1–2 |

Tablets incorporating the above formulations are prepared using conventional methods and materials known in the pharmaceutical art. The resulting nutritional conception composition tablets are recovered and stored for future use.

Example II

The following compositions are used to prepare antinausea products for administration to persons experiencing the symptoms of nausea.

TABLE II

| COMPONENT | FORMULA I | FORMULA II | CHEWABLE FORMULA | CONTROLLED RELEASE |
|---|---|---|---|---|
| Vitamin $B_6$, mg | 20 | 125 | 50 | 125 |
| Vitamin $B_{12}$, mg | 12 | 12 | 12 | 12 |
| Folic Acid, mg | — | 1 | 500 | 1 |
| Calcium Carbonate, mg | 200 | 450 | 200 | 100 |
| Aluminum Hydroxide, mg | — | — | — | 200 |
| Microcrystalline Cellulose, mg | 200 | 200 | — | 200 |
| Ethyl Cellulose Aqueous Dispersion, mg | — | — | — | 180 |
| Croscarmellose Sodium, mg | 18 | 50 | — | 18 |
| Stearic Acid, mg | 50 | 50 | — | 50 |
| Magnesium Stearate, mg | 10 | 10 | 15 | 10 |
| Opadry II, mg | — | 45 | — | 45 |
| Compressible Sugar, mg | — | — | 700 | — |
| Flavor, mg | — | — | 30 | — |

Tablets incorporating the above formulations are prepared using conventional methods and materials known in the pharmaceutical art. The resulting nutritional composition tablets are recovered and stored for future use.

Example III

The following compositions are used to prepare nutritional anti-nausea products for administration to persons experiencing the symptoms of nausea. The components are adjusted based on the body weight of the individual.

TABLE III

| COMPONENT | PER 35 KG OF BODY WEIGHT | PER 55 KG OF BODY WEIGHT | PER 75 KG OF BODY WEIGHT |
|---|---|---|---|
| Vitamin $B_6$, mg | 13–80 | 20–125 | 27–171 |
| Folic Acid, mg | 0.06–1.3 | 0.1–2 | 0.14–2.7 |

Tablets incorporating the above formulations are prepared using conventional methods and materials known in the pharmaceutical art. The resulting nutritional conception composition tablets are recovered and stored for future use.

Example IV

An antinausea and antiemetic formula, as described herein, may further be prepared, as follows:

First, combine a compressible sugar with vitamin $B_6$, and vitamin $B_{12}$ in a blender, and blend until a uniform B vitamin and sugar mixture has been formed. Next, add color and calcium carbonate to the B vitamin and sugar mixture and blend until a uniform B vitamin and calcium carbonate mixture is formed. Then, to the B vitamin and calcium carbonate mixture add microcrystalline cellulose and croscarmellose sodium and mix well until a completely uniform B vitamin and cellulose mixture is reached. To the B vitamin and cellulose mixture add magnesium stearate and blend until a uniform, lubricated B vitamin and cellulose mixture is attained. The lubricated B vitamin and cellulose mixture is then compressed into a tablet using conventional methods. Then the resulting tablets are coated with stearic acid.

Example V

An antinausea and antiemetic formula, as described herein, may further be prepared, as follows:

First, combine a compressible sugar with vitamin $B_6$, vitamin $B_{12}$ and folic acid in a blender, and blend until a uniform B vitamin, folic acid and sugar mixture has been formed. Next, add color and calcium carbonate to the B vitamin, folic acid and sugar mixture. Blend until a uniform B vitamin, folic acid and calcium carbonate mixture is formed. Then, to the B vitamin, folic acid and calcium carbonate mixture add microcrystalline cellulose, croscarmellose sodium, and Opadry II and mix well until a completely uniform B vitamin, folic acid and cellulose mixture is reached. To the B vitamin, folic acid and cellulose mixture add magnesium stearate and blend until a uniform, lubricated mixture is attained. The lubricated mixture is then compressed into a tablet using conventional methods. Then the resulting tablets are coated with stearic acid.

Example VI

A chewable antinausea and antiemetic formula, as described herein, may further be prepared, as follows:

First, combine a compressible sugar with vitamin $B_6$, vitamin $B_{12}$ and folic acid in a blender, and blend until a uniform B vitamin, folic acid and sugar mixture has been formed. Next, add a flavor, color and calcium carbonate to the B vitamin, folic acid and sugar mixture. Blend until a uniform B vitamin, folic acid and calcium carbonate mixture is formed. Then, to the B vitamin, folic acid and calcium carbonate mixture add a compressible sugar and mix well until a completely uniform B vitamin, folic acid and compressible sugar mixture is reached. To the B vitamin, folic acid and compressible sugar mixture add magnesium stearate and blend until a uniform, lubricated mixture is attained. The lubricated mixture is then compressed into a tablet using conventional methods.

Example VII

A controlled release antinausea and antiemetic formula, as described herein, may further be prepared, as follows:

First, combine a compressible sugar with vitamin $B_6$, vitamin $B_{12}$ and folic acid in a blender, and blend until a uniform B vitamin, folic acid and sugar mixture has been formed. Next, add color and calcium carbonate to the B vitamin, folic acid and sugar mixture. Blend until a uniform B vitamin, folic acid and calcium carbonate mixture is formed. Then, to the B vitamin, folic acid and calcium carbonate mixture add aluminum hydroxide, microcrystalline cellulose, ethyl cellulose aqueous dispersion, croscarmellose sodium and Opadry II and mix well until a completely uniform B vitamin, folic acid and cellulose mixture is reached. To the B vitamin, folic acid and cellulose mixture add magnesium stearate and blend until a uniform, lubricated mixture is attained. The lubricated mixture is then compressed into a tablet using conventional methods. Then the resulting tablets are coated with stearic acid.

The invention being thus described, it will be apparent that the same may be varied in many ways. Such variations are not to be regarded as a departure from the spirit and scope of the invention, and all such modifications are intended to be within the scope of the appended claims.

We claim:

1. A anti-nausea nutritional composition which is designed to provide relief from nausea when administered to an animal, which comprises:
   a vitamin $B_6$ compound or derivative thereof in an amount ranging from about 20 mg to 125 mg per 55 kg of said animal's body weight;
   an alkaline buffering agent present in an amount of 100–550 mg and is sufficient to provide a pH buffering effect in said animal's gastrointestinal tract; and
   wherein the composition has a moisture content of less than 5%.

2. The anti-nausea nutritional composition of claim 1, wherein said nausea is associated with pregnancy.

3. The anti-nausea nutritional composition of claim 1, wherein said nausea is associated with motion sickness.

4. The anti-nausea nutritional composition of claim 1, wherein said nausea is associated with allergic reaction.

5. The anti-nausea nutritional composition of claim 1, wherein said nausea is associated with indigestion.

6. The anti-nausea nutritional composition of claim 1, wherein said nausea is associated with stress.

7. The anti-nausea nutritional composition of claim 1, wherein said nausea is associated with a drug side effect.

8. The anti-nausea nutritional composition of claim 1, wherein said nausea is associated with chemotherapy.

9. The anti-nausea nutritional composition of claim 1, wherein the anti-nausea nutritional composition additionally contains a base selected from the group consisting of a chewable base, a quick dissolve base, an effervescent base and combinations thereof.

10. The anti-nausea nutritional composition of claim 1, wherein the alkaline buffering agent is selected from the group consisting of aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

11. The anti-nausea nutritional composition of claim 1, wherein said anti-nausea nutritional composition is an antacid.

12. The anti-nausea nutritional composition of claim 1, wherein the anti-nausea nutritional composition is in an oral dosage form.

13. The anti-nausea nutritional composition of claim 12, wherein the oral dosage form is selected from the group consisting of a chewable tablet, a quick dissolve tablet, an effervescent tablet, a hard gelatin capsule, a soft gelatin capsule, reconstitutable particles, a particulate matrix, microencapsulated particles, a suspension, an elixir, a tablet, a caplet and combinations thereof.

14. The anti-nausea nutritional composition of claim 12, wherein said oral dosage form is selected from the group consisting of a single layer tablet, a multiple layer tablet, particulate matrix tablet and combinations thereof.

15. The anti-nausea nutritional composition of claim 1, wherein said anti-nausea nutritional composition is non-teratogenic.

16. The anti-nausea nutritional composition of claim 1, wherein said anti-nausea nutritional composition additionally contains one or more electrolytes.

17. The anti-nausea nutritional composition of claim 1, wherein said anti-nausea nutritional composition additionally contains a natural plant-derived compound selected from the group consisting of an herb, an herbal extract, a plant extract and combinations thereof.

18. The anti-nausea nutritional composition of claim 1, wherein said anti-nausea nutritional composition is non-emetic.

19. The anti-nausea nutritional composition of claim 1, wherein said anti-nausea nutritional composition is combined with an antiemetic agent.

20. The anti-nausea nutritional composition of claim 19, wherein said antiemetic agent is selected from the group consisting of dimenhydrinate, benzoquinolizine and combinations thereof.

21. The anti-nausea nutritional composition of claim 1, wherein said anti-nausea nutritional composition is combined with an anti-nausea agent.

22. The anti-nausea nutritional composition of claim 1, wherein said anti-nausea nutritional composition is combined with a gastrointestinal agent.

23. The anti-nausea nutritional composition of claim 1, wherein the vitamin $B_6$ compound or derivative thereof is formulated for controlled release, sustained release, extended release, immediate release and combinations thereof.

24. The anti-nausea nutritional composition of claim 1, wherein said composition is administered at least once a day.

25. The anti-nausea nutritional composition of claim 1, wherein said composition is administered at least twice a day.

26. The anti-nausea nutritional composition of claim 1, wherein said composition is divided into at least two fractional doses; and wherein said fractional doses are administered at different times during a 24 hour period of time.

27. A solid anti-nausea nutritional composition which is designed to provide relief from nausea when administered to an animal, which comprises:
   a vitamin $B_6$ compound or derivative thereof in an amount ranging from about 20 mg to 125 mg per 55 kg of said animal's body weight;
   an alkaline buffering agent present in an amount of 100–550 mg and is sufficient to provide a pH buffering effect in said animal's gastrointestinal tract; and
   wherein the composition has a moisture content of less than 5%.

28. The anti-nausea nutritional composition of claim 27, wherein said nausea is associated with motion sickness.

29. The anti-nausea nutritional composition of claim 27, wherein said nausea is associated with allergic reaction.

30. The anti-nausea nutritional composition of claim 27, wherein said nausea is associated with indigestion.

31. The anti-nausea nutritional composition of claim 27, wherein said nausea is associated with stress.

32. The anti-nausea nutritional composition of claim 27, wherein said nausea is associated with a drug side effect.

33. The anti-nausea nutritional composition of claim 27, wherein said nausea is associated with chemotherapy.

34. The anti-nausea nutritional composition of claim 27, wherein said composition is administered at least once a day.

35. The anti-nausea nutritional composition of claim 27, wherein said composition is administered at least twice a day.

36. The anti-nausea nutritional composition of claim 27, wherein said composition is divided into at least two fractional doses; and wherein said fractional doses are administered at different times during a 24 hour period of time.

37. The solid anti-nausea nutritional composition of claim 27, wherein said solid anti-nausea nutritional composition has a moisture content of less than about 5%.

38. An anti-nausea nutritional composition which is designed to provide relief from nausea when administered to an animal, which comprises:
   a vitamin $B_6$ compound or derivative thereof in an amount ranging from about 20 mg to 125 mg per 55 kg of said animal's body weight;
   a folic acid compound or derivative thereof in an amount ranging from about 0.1 mg to 2 mg per 55 kg of said animal's body weight;
   an alkaline buffering agent present in an amount of 100–550 mg and is sufficient to provide a pH buffering effect in said animal's gastrointestinal tract; and
   wherein the composition has a moisture content of less than 5%.

39. An anti-nausea nutritional composition which is designed to provide relief from nausea when administered to an animal, which comprises:
   a vitamin $B_6$ compound or derivative thereof in an amount ranging from about 20 mg to 125 mg per 55 kg of said animal's body weight;
   an alkaline buffering agent present in an amount of 100–550 mg and is sufficient to provide a pH buffering effect in said animal's gastrointestinal tract;
   means for providing pulsed or timed delayed dosing of said vitamin $B_6$ compound or derivative thereof and said alkaline buffering agent; and
   wherein the composition has a moisture content of less than 5%.

40. An anti-nausea and antiemetic nutritional composition which is designed to provide relief from nausea and vomiting when administered to an animal, which comprises:
   a vitamin $B_6$ compound or derivative thereof in an amount ranging from about 20 mg to 125 mg per 55 kg of said animal's body weight;
   an alkaline buffering agent present in an amount of 100–550 mg and is sufficient to provide a pH buffering effect in said animal's gastrointestinal tract; and
   wherein the composition has a moisture content of less than 5%.

41. An anti-nausea nutritional composition which is designed to provide relief from nausea when administered to an animal, which comprises:
   a vitamin $B_6$ compound or derivative thereof in an amount ranging from about 20 mg to 125 mg per 55 kg of said animal's body weight;
   an alkaline buffering agent present in an amount of 100–550 mg and is sufficient to provide a pH buffering effect in said animal's gastrointestinal tract;
   a B vitamin selected from the group consisting of thiamin, riboflavin, niacin, biotin, pantothenic acid, folate, folic acid, cobalamin and combinations thereof; and
   wherein the composition has a moisture content of less than 5%.

42. A method for treating nausea in an animal, which comprises:
   administering to said animal a therapeutically effective amount of a composition comprising:
   a vitamin $B_6$ compound or derivative thereof in an amount ranging from about 20 mg to 125 mg per 55 kg of said animal's body weight;
   an alkaline buffering agent present in an amount of 100–550 mg and is sufficient to provide a pH buffering effect in said animal's gastrointestinal tract; and
   wherein the composition has a moisture content of less than 5%.

43. The method of claim 42, wherein said composition is administered at least once a day.

44. The method of claim 42, wherein said composition is administered at least twice a day.

45. The method of claim 42, wherein said nausea is associated with motion sickness.

46. The method of claim 42, wherein said nausea is associated with allergic reaction.

47. The method of claim 42, wherein said nausea is associated with indigestion.

48. The method of claim 42, wherein said nausea is associated with stress.

49. The method of claim 42, wherein said nausea is associated with a drug side effect.

50. The method of claim 42, wherein said nausea is associated with chemotherapy.

51. A method for treating nausea or vomiting in a pregnant woman, which comprises:
   administering to said pregnant woman a therapeutically effective amount of a composition comprising a vitamin $B_6$ compound or derivative thereof in combination with an alkaline buffering agent.

52. A method for treating nausea in a pregnant woman, which comprises:
   administering to said pregnant woman a therapeutically effective amount of a composition comprising a vitamin $B_6$ compound or derivative thereof in combination with an alkaline buffering agent; and
   simultaneously applying controlled pressure to an acupressure site on said pregnant woman.

53. A method for treating hyperemesis gravidarum in a pregnant woman, which comprises:
   administering to said pregnant woman a therapeutically effective amount of a composition comprising a vitamin $B_6$ compound or derivative thereof in combination with an alkaline buffering agent.

54. A method for treating a patient predisposed to nausea associated with pregnancy, which comprises:
   administering in combination with a prenatal vitamin regimen a composition comprising a vitamin $B_6$ compound or derivative thereof in an amount ranging from about 20 mg to 125 mg per 55 kg of said animal's body weight and an alkaline buffering agent in an amount sufficient to provide a pH buffering effect in said animal's gastrointestinal tract.

55. A kit for treating nausea or vomiting in an animal, which comprises:
  a vitamin $B_6$ compound or derivative thereof in combination with an alkaline buffering agent; and
  an apparatus for applying controlled pressure to an acupressure site on said animal.

* * * * *